April 20, 1976 R. S. MOORE Plant Pat. 3,869
MINIATURE ROSE PLANT
Filed Jan. 30, 1975
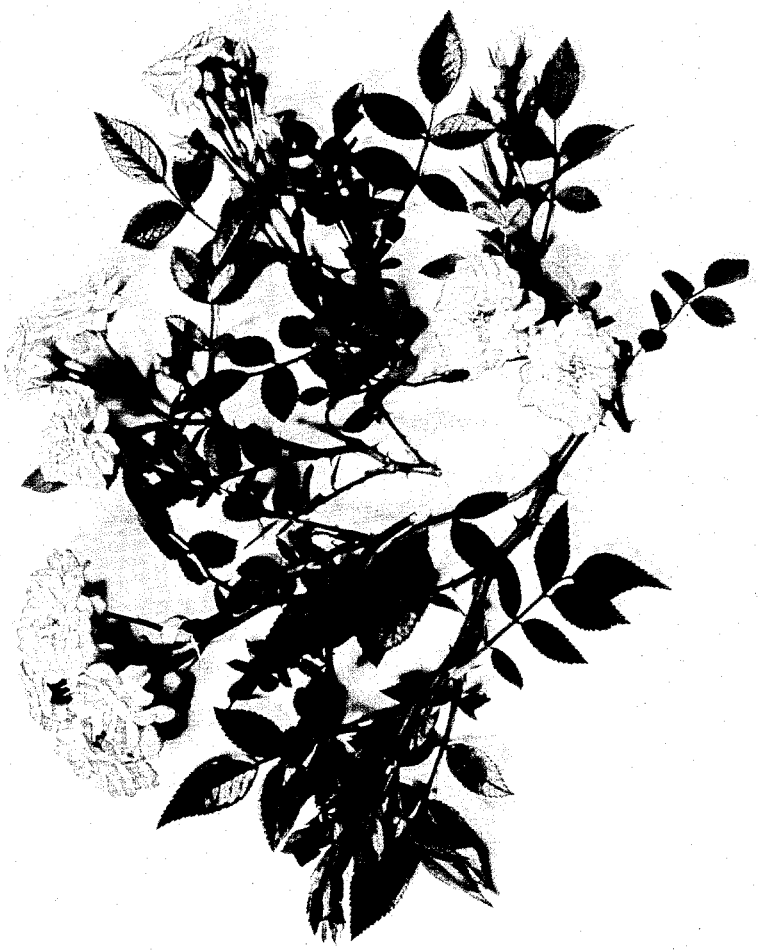

United States Patent

Plant Pat. 3,869
Patented Apr. 20, 1976

3,869
MINIATURE ROSE PLANT

Ralph S. Moore, 2519 E. Noble Ave.,
Visalia, Calif. 93277

Filed Jan. 30, 1975, Ser. No. 545,723
Int. Cl. A01h *5/00*
U.S. Cl. Plt.—9 1 Claim The present invention relates to a new and distinct variety of hardy, dwarf, bush type rose plant of the miniature class; the variety being primarily characterized—as to novelty—by pink buds and flowers which in general color effect are medium to light pink with a slight lavender cast, similar in color to (but deeper) Ellen Poulsen (polyantha—not patented).

The variety is further characterized by:

An abundance of bloom, with flowers generally borne in clusters of 3 to 5 or more to the stem.

Little or no fragrance.

A plant which is vigorous, of rounded spreading shape and with small, medium green, glossy foliage with pointed leaflets; the buds and flowers being similar in form and size to Dian (miniature—Plant Pat. 1,808). The plant, which has a normal height of 6–9 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Ellen Poulsen (polyantha—not patented) as the seed parent and Little Chief (miniature—not patented) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identification being by reference to the British Colour Council Horticultural Colour Chart, except where common terms of color definition are employed.

Type: Hardy; dwarf; bush; seedling; greenhouse; outdoors; cut flowers; garden decoration potted plant.

Class: Miniature.

Flowers: Continuity continuous—repeat bloom all season—fragrance; little or none.

Flowers borne: Several together in clusters on slender, short stems.

Quantity of bloom: Abundant both outside and in greenhouse.

Bud: Peduncle—short; slender but sturdy; erect; medium green.

Hairs—usually none. Before calyx breaks: size—small. Form—short pointed to globular; with few or no foliaceous appendages and usually no hairs on surface of bud; with foliaceous parts extending beyond the tip of the bud equal to less than one half of its length. Color—Medium green. As calyx breaks: color—reddish, often with some green at base. As first petal opens: same general color; size—small.

Bloom:

*Size when fully open.*—Small, averaging about 1" (25–28 mm.).

*Petalage.*—Double, 40–50 petals (plus several small petaloids) arranged irregularly.

*Form.*—Very full; petals rolled loosely outward.

Petals: Fairly thick; satiny on both inside and outside surfaces.

*Shape.* — Outside petals, broad lanceolate with rounded tip;

*Intermediate.*—Broad lanceolate with rounded tip;

*Inside.*—Lanceolate.

Color: Newly opened flower from a plant grown in plastic greenhouse (January 1975), Visalia, Calif.

*Outside petal.*—Outside surface—Fuchsine Pink 627/1, shading into near white on lower one-third of petal; Inside surface—Fuchsine Pink 627/1, blending into near white on lower one-fourth of petal.

*Intermediate petal.*—Outside surface—Fuchsine Pink 627/1, blending into near white on lower one-fourth of petal; Inside surface—Fuchsine Pink 627/1, blending into near white on lower one-fourth of petal.

*Inner petal.*—Outside surface.—Fuchsine Pink 627/1, blending into near white on lower one-fourth of petal. Inside surface—same as outside surface.

*General color effect of newly opened flowers.*—Medium pink with soft lavender tint.

*Three days open.*—About same color.

*Behaviour.*—As flowers age color may become lighter shade.

*Flower longevity (September, 1974) bush in garden or pot.*—5–6 days or longer. Cut flowers at living room temperature—4–5 days.

Reproductive organs:

*Stamens.*—Few or none.

*Filaments.*—Short; color yellow (if present).

*Anthers.*—Yellow.

*Pollen.*—Scarce or none.

*Pistils.*—Few to average number.

*Styles.*—Fairly even; bunched; color—greenish.

*Ovaries.*—All enclosed.

*Hips.*—None.

*Seeds.*—None.

Foliage:

*Leaves.*—Compound of five, often seven, leaflets; abundant; small; leathery; glossy.

*Leaflets.*—Shape: Lanceolate; apex acute; base less acute. Margin: serrate. Color: normal green. Rachis: Medium long; narrow to medium width; grooved, with several small thorns or prickles on lower edge.

*Stipules.*—Medium long; medium width; narrow points may turn out at an angle of more or less than 45 degrees.

Growth:

*Habit.* — Dwarf; very bushy; rounded; much branched, tending to grow broader than tall.

*Growth.*—Free; vigorous.

*Canes.*—Medium; sturdy; slender.

*Main stems.*—Color: medium green. May darken with age.

*Thorns.*—Quite thorny; medium length; curved downward; color—brown.

*Prickles.*—None; Hairs: none.

*Branches.* — Color — medium green; thorns — quite thorny; medium length; slender; curved downward.

Relatively long oval base. Prickles—none; hairs—none.

*New shoots.*—Color—medium green. Thorns: quite thorny; medium length; slender; curved downward; base oval. Prickles: none; hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Dian miniature rose (Plant Pat. 1,808) in general form of bud and flower, the color, generally, being a lighter shade of pink with often a magenta or lavender tint and the petals tending to be more numerous, the general color effect being medium to lighter pink; and further characterized by a plant which is vigorous in growth, of dense compact habit, tending to become more wide than tall, easy to propagate from cuttings; with small, glossy, disease resistant foliage; the plant tending to flower profusely, in clusters, even when very small.

No references cited.

ROBERT E. BAGWILL, Primary Examiner